United States Patent
Augustine et al.

[11] Patent Number: 5,837,002
[45] Date of Patent: Nov. 17, 1998

[54] SUPPORT APPARATUS WITH LOCALIZED COOLING OF HIGH-CONTACT-PRESSURE BODY SURFACE AREAS

[75] Inventors: Scott D. Augustine, Bloomington; Paul Anthony Iaizzo, White Bear Lake; Ephraim M. Sparrow, St. Paul; Paul Steven Johnson, White Bear Lake; Randall C. Arnold, Minnetonka; Donald E. Stapf, Minneapolis, all of Minn.

[73] Assignee: International Business Machines Corporation, Armonk, N.Y.

[21] Appl. No.: 704,887

[22] Filed: Aug. 30, 1996

[51] Int. Cl.⁶ .................................................... A61F 7/00
[52] U.S. Cl. ............................. 607/104; 5/421; 607/108; 607/114
[58] Field of Search ..................... 607/96, 104, 107–112, 607/114; 165/46; 5/421–423; 297/284.6, 452.57, 542.27, 452.41; 126/204

[56] References Cited

U.S. PATENT DOCUMENTS

| | | | |
|---|---|---|---|
| 3,289,748 | 12/1966 | Jennings . | |
| 3,421,163 | 1/1969 | Stoughton | 297/452.41 |
| 3,738,702 | 6/1973 | Jacobs | 165/105 |
| 4,026,299 | 5/1977 | Sauder | 128/400 |
| 4,114,620 | 9/1978 | Moore et al. | 128/254 |
| 4,149,541 | 4/1979 | Gammons et al. | 128/400 |
| 4,416,281 | 11/1983 | Cooper et al. | 128/400 |
| 4,706,672 | 11/1987 | Jones | 128/379 |
| 4,844,072 | 7/1989 | French et al. | 128/400 |
| 4,884,304 | 12/1989 | Elkins | 5/421 |
| 4,886,063 | 12/1989 | Crews | 607/112 |
| 4,962,761 | 10/1990 | Goldent | 128/400 |
| 4,966,145 | 10/1990 | Kikumoto et al. | 128/377 |
| 5,072,875 | 12/1991 | Zacoi | 128/400 |
| 5,097,829 | 3/1992 | Quisenberry | 128/400 |
| 5,138,138 | 8/1992 | Theilacker et al. | 219/528 |
| 5,169,384 | 12/1992 | Bosniak et al. | 604/20 |
| 5,174,285 | 12/1992 | Fontenot | 128/400 |
| 5,176,424 | 1/1993 | Tobita et al. | 297/284 |
| 5,183,039 | 2/1993 | Sarian et al. | 128/400 |
| 5,269,369 | 12/1993 | Faghri | 607/104 |
| 5,344,436 | 9/1994 | Fontenot et al. | 607/104 |
| 5,433,083 | 7/1995 | Kuramarohit | 62/259 |
| 5,448,788 | 9/1995 | Wu | 5/421 |
| 5,456,701 | 10/1995 | Stout | 607/104 |
| 5,486,206 | 1/1996 | Avery | 607/104 |
| 5,556,169 | 9/1996 | Parrish et al. | 297/452.41 |
| 5,632,051 | 5/1997 | Stanley et al. | 5/421 |

OTHER PUBLICATIONS

"Prevention of Pressure Ulcers by Focal Cooling: Histological Assessment in a Porcine Model", Paul A. Iaizzo, Ph.D. et al., *WOUNDS: A Compendium of Clinical Research and Practice*, Sep./Oct. 1995, vol. 7, No. 5, pp. 161–169.

"Designed By Critical Care Physicians And Nurses With The Patient In Mind" brochure, TriaDyne by KCI.

*Primary Examiner*—Jeffrey R. Jastrzab
*Assistant Examiner*—Ryan Carter
*Attorney, Agent, or Firm*—Gray Cary Ware Freidenrich

[57] ABSTRACT

A focal cooling apparatus includes a cooling, or heat sinking, layer over which a layer of compressible, thermally insulating material is disposed. The layer of compressible, thermally insulating material has a surface for supporting a portion of a human (or animal) body. The layer of compressible, thermally insulating material responds to pressure exerted against the surface by exhibiting a thermal resistance between the surface and the cooling layer that varies inversely with the pressure. Means are provided for maintaining the cooling layer at a predetermined temperature below normal human temperature.

25 Claims, 4 Drawing Sheets

FIG. 12 ly develop near regions of the body which have a bony prominence near the skin. More than 80% of all pressure ulcers occur at the following five locations:
SUPPORT APPARATUS WITH LOCALIZED COOLING OF HIGH-CONTACT-PRESSURE BODY SURFACE AREAS

BACKGROUND OF THE INVENTION

1. Field of the Invention

The invention concerns an apparatus for supporting at least a portion of a human or animal body with cooling localized at or focused on the weight-bearing areas of the portion. The localized, or focused, cooling reduces the risk of damage to the weight-bearing body areas of patients confined to beds, operating room tables, or wheelchairs for long periods of time.

The application of pressure to the skin of a patient for a prolonged period of time has been known to cause pressure ulcers or pressure ulcers. The weight-bearing areas of the body surface are exposed to pressures that can easily exceed 100 mmHg (torr.). It has been shown that blood flow ceases in capillaries that are exposed to compressive pressures exceeding 25 torr. Therefore, the weight-bearing areas of the body surface and subcutaneous tissue can be expected to have inadequate blood flow or even a complete lack of blood flow during the time the weight is borne.

Normal cellular metabolism depends on adequate circulation of blood to deliver oxygen, nutrients and to remove waste products. Prolonged interference with the local circulation results in a two-part sequence of events, beginning with ischemia (a severe reduction of blood and oxygen supply to the tissues) and terminating in necrosis (irreversible death of the cells and tissues, resulting in sloughing).

People normally will shift their positions in a chair or get up and walk around to relieve the pressure on their buttocks. People normally will regularly roll over in bed while sleeping to periodically redistribute their weight to a different surface area. This movement is usually in response to pain or discomfort caused by the tissue ischemia of the weight-bearing skin, subcutaneous or deeper tissue. Bed-ridden or wheelchair-ridden patients or patients on operating room tables may not be aware of the ischemic pain if they have brain or spinal cord injury, stroke injury, dementia, prolonged surgery under anesthesia, or prolonged sedation and mechanical ventilation. Alternatively, severe illness, neuromuscular diseases or nervous system injury may prevent patients from moving even if they are aware of the ischemic pain.

The incidence of pressure ulcers in surgical patients varies from 12% to 66% in different studies. Surveys of general hospital patients indicate that 3–4.5% of all patients develop pressure ulcers during hospitalization. Pressure ulcers usually develop near regions of the body which have a bony prominence near the skin. More than 80% of all pressure ulcers occur at the following five locations:

1. Sacro-coccygeal region (high buttocks), supine position.
2. Greater trochanter (low hip), lateral recumbent position.
3. Ischial tuberosity (low buttocks), sitting position.
4. Tuberosity of the calcaneus (heel), supine position.
5. Lateral malleolus (outer ankle), lateral recumbent position.

Surgical and bed ridden patients are not the only patients susceptible to pressure ulcer development. For example, paralyzed patients spend much of their lifetime in a wheelchair. One study indicated that the incidence of pressure ulcers is 21.6% for paraplegics and 23.1% for quadriplegics.

Equipment for pressure ulcer prevention has focused in three areas:

1. Regular turning or movement of the patient to minimize the duration of time that pressure is applied to any give surface area. The tissue is allowed time to re-perfuse during the period that the pressure is not applied.
2. Passive support surfaces (cushions, mattresses and pads of all kinds), which may utilize unique or special materials or shapes to minimize the pressure exerted against any given point of the body surface. Many types of materials have been tried including; different types of polymeric foam, polymeric gels, water and air filled bladders.
3. Active support surfaces such as a series of air filled bladders that alternately inflate and deflate to automatically redistribute the pressure.

Considering the high incidence of pressure ulcers despite the availability of these many passive support surfaces (various materials and shapes), it is clear that simply distributing the pressure to a larger surface area, in and of itself, will not effectively prevent pressure ulcers. Although active support surfaces have been used to prevent pressure ulcers, it is clear that they are very expensive, cumbersome and noisy. Therefore active support surfaces are not likely to be used in many pressure ulcer prevention situations.

Finally, aside from the obvious pain and health risk to the patient (having a chronic infection in a chronic open wound), pressure ulcers are extremely expensive and slow to heal. Healing the average pressure ulcer costs $30,000 to $40,000 and takes about 3 to 6 months. The high incidence of pressure ulcers, the lack of any proven method of preventing pressure ulcers and the extremely high cost of healing a pressure ulcer once it develops, clearly indicates a significant need for a new technology.

It is reasonable to assume that heat should be an important factor in the formation of pressure ulcers. All tissues increase their metabolic rates 7–10% for each 1° C. increase in temperature. The increased metabolic rate increases the demand of the cells for oxygen a similar 7–10% for each 1° C. increase in temperature. In a patient whose tissue perfusion is already compromised by external pressure or by vascular insufficiency, this increased metabolic demand for oxygen could increase the rate of tissue injury. We hypothesized that this increased metabolic demand was the cause of the frequent "burns" observed after water mattress warming therapy during surgery, despite the relatively low temperatures (39°–42° C.) of the mattresses. These low temperature injuries may result in full thickness skin damage which appears identical to third degree burns resulting from exposure of the skin to high temperatures. While the full thickness damage to the skin is identical to a high temperature thermal injury ("burn"), in reality the injury is caused by pressure necrosis which is accelerated due to the increased metabolic rate of the tissue. While this interrelationship between temperature, pressure and tissue ischemia is scientifically logical, it had never been proven prior to our recent experiments.

Further, it is known that hypothermia decreases the cellular metabolic rate and increases the tolerance of cells to periods of inadequate blood flow. This is the reason that patients are cooled during cardiac bypass. We therefore hypothesized that cooling the skin and subcutaneous tissue would effectively prolong the time to injury, in the face of the ischemia caused by an inadequate local blood flow resulting from pressure exerted against that tissue.

To test these hypotheses, we developed a porcine model to investigate pressure ulcer formation. Twelve metal discs were applied to the back of an anesthetized swine. The pressure on the skin under each disc was approximately 100 torr (totally occlusive to blood flow), for a 10 hour period of time. The temperature of the discs was carefully controlled at 25° C., 35° C., 40° C. and 45° C. Normal porcine body temperature is 38° C. (Normal human body temperature is 37° C.) The severity of the resultant tissue injuries directly correlated with an increase in temperature. No tissue damage was found under the 25° C. discs. Severe damage of the skin, subcutaneous and deep tissues was found under the 45° C. discs. The 35° and 40° C. discs also caused severe damage, but intermediate to the extreme temperatures. The results of this experiment strongly indicated that both of our hypotheses were correct:

1. Even mild heat will accelerate the rate of tissue injury due to pressure induced ischemia.
2. Mild cooling will protect tissue from injury due to pressure induced ischemia.

Water mattresses circulating cool or even cold water have been used for decades to cool febrile patients. However, experience shows that the application of cold to widespread surface areas of the body is both extremely uncomfortable and will cause hypothermia and shivering.

2. Description of the Related Art

In the prior art, U.S. Pat. No. 3,738,702 discloses a seat structure that cools a portion of the human body that rests against the seat in response to the heat of the body, where the body engages the seat. In order to maximize the sensitivity of the cooler to body heat, the cooler is placed as near as possible to the surface of the seat contacted by the body.

SUMMARY OF THE INVENTION

The object of this invention is to provide a bed mattress, an operating room table cushion, or a chair or wheelchair cushion that can automatically sense the specific areas of "high" contact pressure (greater than 20–25 torr, for example) and selectively apply cooling to (or, more precisely, remove heat from) those specific areas.

In supine or sitting patients, metabolic heat generated by the ischemic tissue is trapped by padded cushions or mattresses and raises the tissue temperature. The metabolic heat cannot be internally removed because of the inadequate blood flow and cannot be externally removed because of the thermal insulation characteristics of the padded cushions or mattresses. Metabolism continues (anaerobically) despite the inadequate blood flow, and the heat generated by this metabolism continues to accumulate. Our swine studies show that any warming of tissue is clearly harmful and cooling of the tissue below body temperature is beneficial in preventing pressure injury to tissue. Cooling below normal body temperature will be beneficial. Therefore this invention alleviates or prevents the buildup of naturally generated metabolic body heat in the ischemic tissue in weight-bearing areas of a body supported by a padded cushion or mattress. The adjacent body surface areas which are not experiencing high pressure will not be cooled. Because of the minimal blood flow in the areas of high pressure, the cooling effect will be substantially isolated to those tissues and not cause total body hypothermia or discomfort.

Our invention is based upon the critical observation that the application of cooling to (or removal of heat from) those areas of a body that are subject to the greatest risk of ischemia in bearing the weight of the body may have cooling selectively applied by an apparatus with a heat conveying (or, heat transmitting) path that exhibits decreased thermal resistance in inverse proportion to pressure. In this regard, if a surface of the apparatus is the same as that which supports the body, force exerted against the surface by a weight-bearing area of the body would compress the heat conveying pathway beneath the weight-bearing area of the body, making the pathway shorter, and therefore more conductive (less resistive) to the flow of heat than beneath a portion of the surface that bears relatively less of the body's weight.

With greater specificity, our invention is an apparatus that localizes or focuses cooling applied to a supported human body by concentrating (focusing) the cooling on those areas of the body bearing the body's weight.

More specifically, the focal cooling apparatus of our invention includes a cooling, or heat sinking, layer over which a layer of compressible, thermally insulating material is disposed. The layer of compressible, thermally insulating material has a surface for supporting a portion of a human (or animal) body. The layer of compressible, thermally insulating material responds to weight brought against the surface by providing a thermal resistance between the surface and the cooling layer that varies inversely with the pressure. Means are provided for controlling the cooling layer to maintain a predetermined temperature that is below normal human body temperature.

Accordingly, it is an objective of this invention to provide an apparatus that localizes cooling of high contact-pressure body surface areas which bear the weight of the body.

A further objective is the provision of an apparatus that supports a human body while selectively cooling those portions of the body in contact with the apparatus that bear relatively greater amounts of the body's weight than other areas in contact with the apparatus.

Advantageously, the apparatus inherently finds the specific areas of the human body subject to relatively high contact pressure and selectively applies cooling to those specific areas.

In another view of the advantage, the apparatus inherently finds the specific areas of high contact pressure and selectively removes heat from those areas.

These and other objects and advantages of this invention will become clearer when the following detailed description is read with reference to the below-described drawings.

DETAILED DESCRIPTION OF THE PREFERRED EMBODIMENTS

Figure 1:
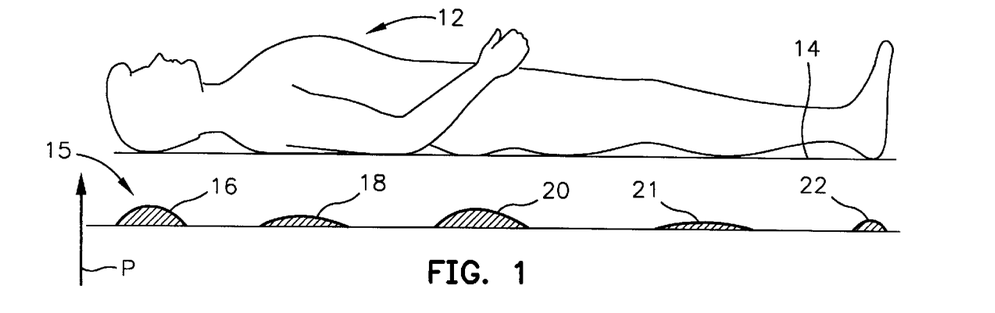
FIG. 1 illustrates a supine person and a plot showing pressure exerted on weight-bearing portions of the person's body by a surface that supports the body.

With reference now to the figures which illustrate this invention and in which like parts are designated by like reference numerals throughout the drawings, FIG. 1 shows a supine person 12 resting on, which is to say supported by, a surface 14. Directly underneath the surface 14 is a plot 15 that represents pressure measured at the surface 14. The pressure is exerted by the weight-bearing portions of the body and has its peak magnitude in those areas where the body 12 contacts the surface 14. Note particularly that distinct pressure distributions are exhibited for the back of the head at 16, the upper back at 18, the buttocks at 20, the calves at 21, and the heels at 22. (The contributions of the elbows are not shown.) These are the areas of the body which bear much of the weight of the person, and they are referred to as "weight-bearing" areas. Manifestly, if the supine person 12 is bed-ridden, the weight-bearing areas that the buttocks and heels are at most risk for pressure injury.

The invention, in its structure and operation, takes into account and exploits the distribution of pressure exerted by a support surface on the weight-bearing areas of a human or animal body. Advantage is taken of local pressure elevation in this regard by reducing the thermal resistance of a thermally insulating layer between a cooling layer and one or more portions of the support surface where weight-bearing areas of a supported human or animal body are borne. This principle is embodied preferably in an apparatus illustrated by the partially schematic, longitudinal sectional drawings of FIGS. 2–4.

Figure 2:
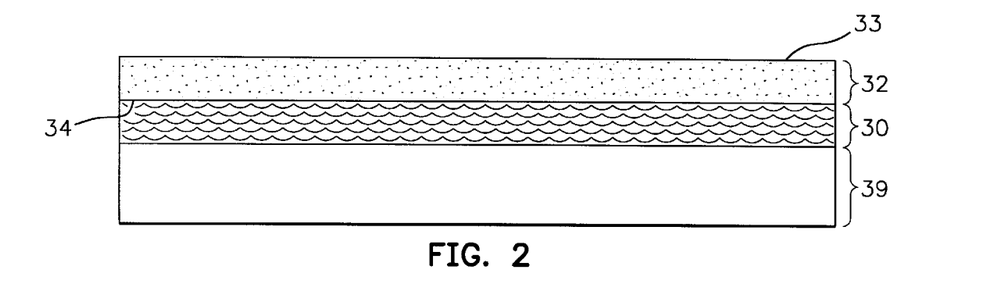
FIGS. 2 and 3 illustrate a preferred embodiment of the invention in a longitudinal, partially schematic section.
Figure 3:
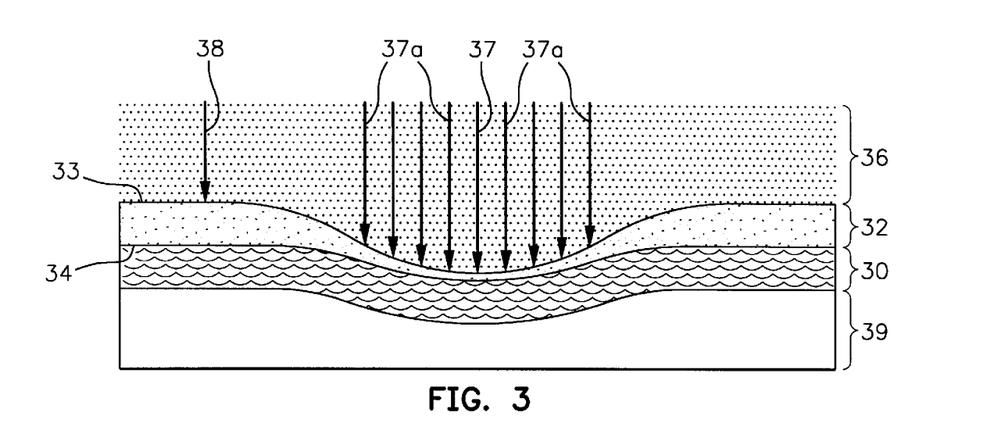
Figure 4:
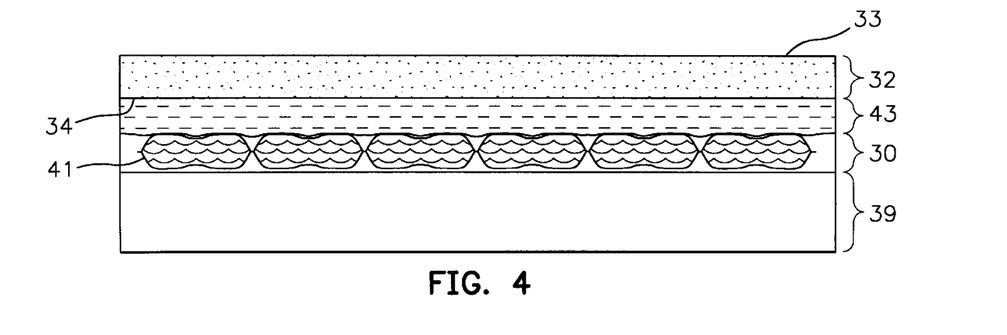
FIG. 4 illustrates an option to the preferred embodiment in a longitudinal, partially schematic section.

In FIGS. 2–4, an apparatus for supporting at least one portion of a human or animal body includes a cooling layer 30 over which is disposed a layer 32 of compressible, thermally-insulating material that is in thermal contact with the cooling layer. Such thermal contact may comprise direct physical contact between the layers 30 and 32 or through a thermally conductive intermediary, as described below. The layer 32 includes an upper surface 33 and a lower surface 34.

The essential operation of the invention is shown in FIG. 3 where a weight-bearing area on a portion of the human body, say for example the buttocks, represented by shaded area 36 exerts a relatively greater pressure represented by the arrow 37 on a portion of the surface 33 under and around the weight-bearing area than under the area of the body that produces the pressure magnitude represented by the arrow 38. In fact, as the arrows 37a indicate, the weight-bearing area exerts a varying pressure or pressure distribution on the surface 33 that presses it toward the surface 34. In response to the greater pressure exemplified by the arrow 37, the portion of the compressible, thermally-insulating layer 32 under the portion of the surface 33 that bears the greater pressure 37 (and the pressure distribution 37a) has been compressed and exhibits a smaller cross-sectional height than the portion underneath the portion of the surface 33 that receives the pressure 38. In fact, as FIG. 3 makes clear, the compression of the layer 32 under the pressure distribution 37a exhibits a profile corresponding to the distribution 37a. The smaller cross-sectional height in the portion of the layer 32 that is compressed reduces the magnitude of thermal resistance as compared to the magnitude of thermal resistance of the portion of the layer 32 that supports the pressure 38. In fact, the compressed portion has a thermal resistance distribution that varies approximately as the inverse of the pressure distribution. The lower magnitude of thermal resistance results from reduction in the length of the thermally conductive path between the surfaces 33 and 34 to the cooling layer 30, as well as alteration of other thermal characteristics caused by compression of the layer 32. The reduced thermal resistance is equivalent to an enhanced thermal conductivity through the layer 32 between the weight-bearing area of the body represented by the shaded area 36 and the cooling layer 30, at a portion of the surface 33 that is contiguous with the weight-bearing area of the body. Providing the cooling layer 30 with the ability to locally cool the body to a temperature that is below the normal temperature of the body represented by shaded area 36 will result in a localization or focusing of cooling at the weight-bearing area of the body bearing against the surface 33. Conversely, the relatively higher level of thermal resistance of the layer 32 under those areas of the body represented by the shaded area that exert little or no pressure will prevent those body areas from being cooled at rates comparable to the cooling rates at weight-bearing areas. This accomplishes the objective of localization or focusing of cooling at the weight-bearing areas of a supported body, without inducing total body hypothermia and shivering.

Preferably, as shown in FIGS. 2 and 3, the layer 32 of compressible, thermally insulating material is formed from a material that is compressible in response to pressure but "remembers" its original shape, which it reassumes when the pressure is released. Similarly, the cooling layer 30 has the ability to deform in order to adapt itself to the shape of the weight-bearing portion of the body, but also "remembers" its undeformed shape and resumes it when the pressure is removed.

In the preferred embodiment, the layer 32 of compressible, thermally insulating material preferably includes a foam insulating pad that may be made, for example, from polymeric open-cell foam plastic, or foam rubber having an uncompressed thickness of 0.5"–1.0". In its normal uncompressed state, this thickness provides significant thermal insulation between the surfaces 33 and 34 to the cooling layer 30. Because it is compressible, under the weight-bearing portions, the thickness, the thermal resistance, and the thermal insulating capability of the foam pad are reduced. The intrinsic compressibility and resiliency of the foam material selected to form the layer 32 of compressible, thermally insulating material would determine how much pressure must be applied in any portion of the surface 33 to compress the material to some minimal thickness.

To enhance the thermal conductivity of the layer 32 where it compresses, a small amount of water or other liquid such as glycol can be interspersed in the material of the layer 32. Preferably, the amount does not saturate the layer when uncompressed, but does saturate the layer where it is compressed. When not compressed, the liquid will have little effect on the thermal resistance of the layer 32.

The cooling layer 30 acts essentially as a heat sink that increases the magnitude of the temperature difference between the surface 33 and itself, across the layer 32 of compressible, thermally heat insulating material. The cooling layer 30 can comprise, for example, a flexible water mattress in which cooled water, below normal body temperature (that is below 37° C.), is circulating. While the term "water mattress" is used, those skilled in the art will appreciate that many different fluids could be circulated through this layer with a similar cooling effect. Such fluids include, for example, glycol-water mixtures, alcohol-water mixtures, air, and other fluids. The water mattress can comprise a standard water mattress available from, for example, Cincinnati Sub Zero Products, Cincinnati, Ohio, or Gaymar Industries, Orchard Park, N.J. These mattresses are typically made of two sheets of flexible polyethylene or polyvinyl film, thermoformed into a parallel array or labyrinth of fluid channels, and then heat sealed together. Water is circulated through the mattresses by an external pump with cooling capabilities. Circulating cool water causes the water mattress to operate as a heat sink. The heat absorbed into the fluid circulating in the mattress is ultimately dissipated into a secondary heat sink, which is usually ambient air. Typically, such an arrangement may require tubing for circulation of water to and from the water mattress, a pump, a receiver, and a cooling means (all of which are not shown in FIGS. 2–4). The cooling means can be compression-based, thermoelectric based, radiator/air based, heat exchanger/ice based, or based on any other suitable method of cooling the circulating fluid.

Alternatively, the cooling layer 30 can be a mattress or pad made of heat-absorbing, phase-change material. Many salt solutions and paraffins are known to have such a characteristic. The desired temperature of the phase-change can be achieved by selecting the appropriate combination of salts and solvents.

An additional, optional element of the apparatus illustrated in FIGS. 2–4 is a support layer 39 that can comprise a mattress or pad of some compressible, resilient construction and/or material. If elected, the support layer 39 is positioned under, and supports, the cooling layer 30 and the layer 32 of compressible, thermally insulating material such that the layer 30 is sandwiched between the layer 32 and the support layer 39.

In FIG. 4, another optional, added element is illustrated. FIG. 4 is a longitudinal sectional, partially schematic drawing that illustrates the structure of the cooling layer 30 embodied in a multi-channel water mattress that comprises a plurality of adjacent channels, typified by the channel 41. Because the water mattress of the cooling layer 30 presents an irregular upper surface, a "smoothing" layer 43 is added between the layer 32 of compressible, thermally insulating material and the cooling layer 30. The smoothing layer 43 may comprise a thin pad that evens out the irregular surface of the water mattress of the cooling layer 30. The smoothing layer 43 may include a thin pad containing a thermally conductive material such a polymeric gel, water, or another fluid. Preferably, the layer 43 is compliant, deforming in response to pressure and resuming its original configuration when the pressure is released.

Figure 5:
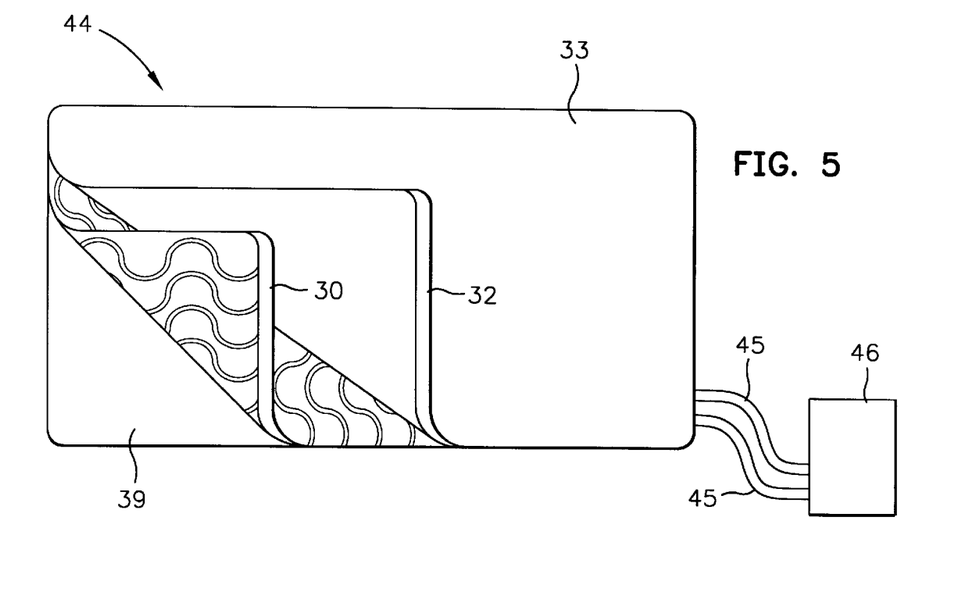
FIGS. 5 and 6 illustrate a support pad or mattress assembled according to the preferred embodiment, with FIG. 5 being a top, plan view with layers folded back for visualization and FIG. 6 being a perspective view with the layers folded back for visualization.
Figure 6:
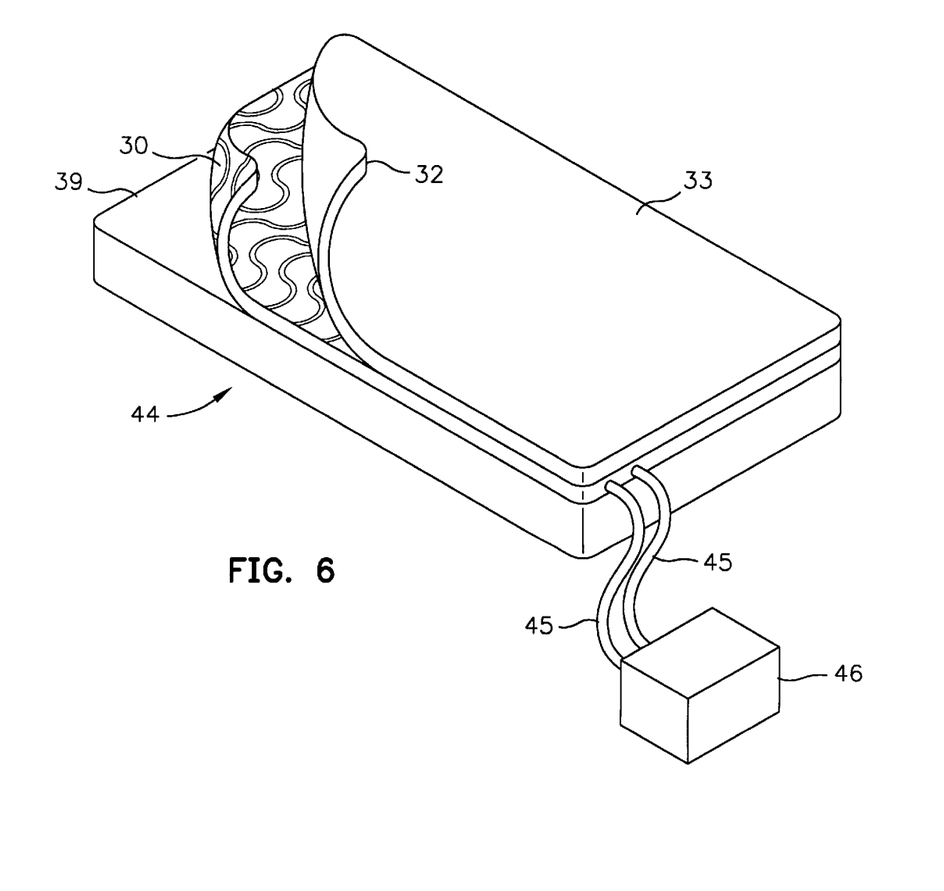

Refer now to FIGS. 5 and 6 which show an article of manufacture such as a support pad or mattress that incorporates the invention as expressed in the first embodiment shown in FIGS. 2–4 or the embodiments discussed below. In the figures, the article of manufacture 44 includes the cooling layer 30 in the form a water mattress with serpentine channels sandwiched between the layer 32 of compressible, thermally insulating material and the support mattress 39. The elements 30, 32 and 39 can be joined together by means known in the art such as gluing, stitching, enclosing in a thin-walled coverlet pocket, and so on. Means for maintaining the temperature of the cooling layer 30 at a predetermined temperature, for example below normal human body temperature, are provided by the tubes 45 and the cooling apparatus 46. The tubes 45 are in fluid communication with the serpentine tubes of the water mattress of which the cooling layer 30 is comprised. The tubes 45 connect to the cooling apparatus 46, which operates according to any of the cooling techniques described above with reference to FIGS. 2–4. The cooling apparatus 46 for example may comprise a compressor-based refrigerator, a thermo-electric based refrigerator, a Stirling-cycle cooler, a radiator, or a heat exchanger.

Figure 7:
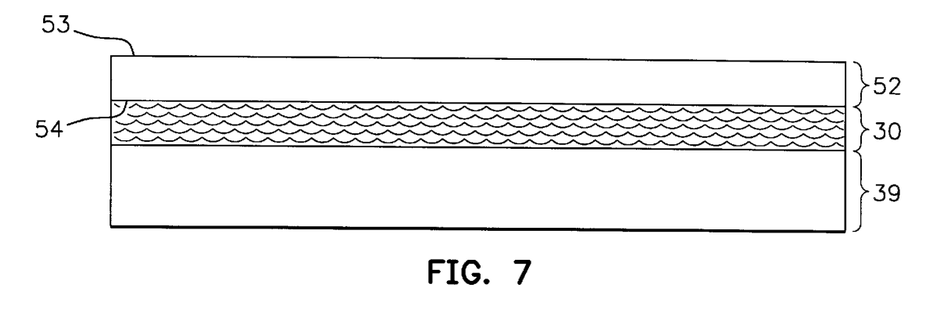
FIGS. 7 and 8 illustrate a first alternate embodiment of the invention in a longitudinal, partially schematic cross-section.
Figure 8:
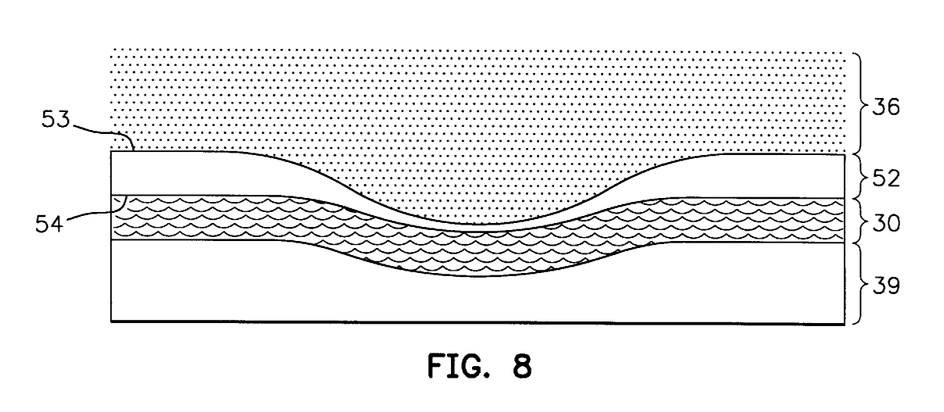
Figure 9:
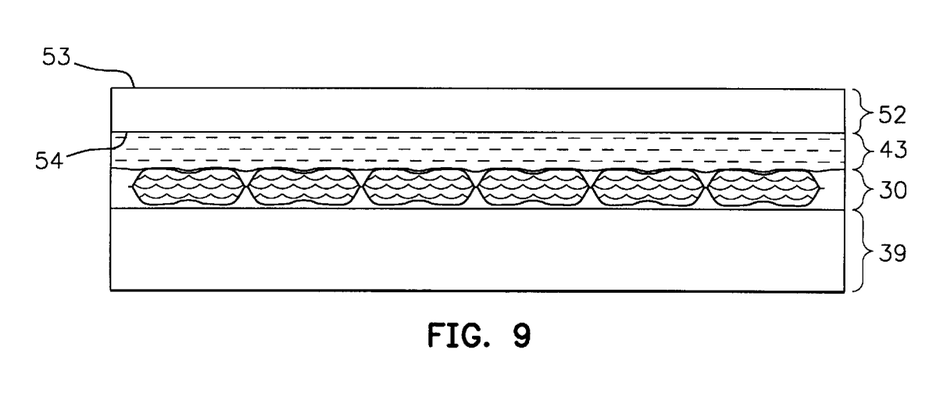
FIG. 9 illustrates an option to the first alternate embodiment in a longitudinal, partially schematic section.

FIGS. 7 and 8 show a first alternate embodiment of the invention in longitudinal sections; FIG. 9 shows an option to the first alternate embodiment in a longitudinal section. In the first alternate embodiment, the layer 32 of insulating material, discussed above with respect to FIGS. 2–6, is specifically embodied in gas-filled bladder insulating pad 52 that is disposed over the cooling layer 30, which preferably is in the form of a flexible water mattress in which cooled water, below normal human body temperature (below 37° C.) is circulating. Preferably, but not necessarily, the bladder 52 and cooling layer 30 are disposed on the support structure 39.

The bladder 52 is preferably made of a polymeric film or synthetic woven material, or comprises a laminant of the two materials and, when filled with a gas such as air, has a thickness sufficient to provide significant thermal insulation between the cooling layer 30 and a surface 53 of the bladder 52 that supports one or more portions of a human or animal body. For example, the thickness of the bladder 52 when filled with air can be from 1.0" to 2.0". The gas in the bladder 52 is preferably under slight pressure, and may or may not be circulating through the bladder. Manifestly, the bladder 52 must be compressible (that is, comprised of compressible air contained in an extensible material) so that, under the weight-bearing areas of a human or animal body, its surface 53 will be pressed toward its surface 54, thereby reducing its thermal resistance. FIG. 8 shows how the buttocks of a patient represented by the shaded area 36 compresses the bladder 52. Clearly the thermal resistance of the gas in the bladder 52 is reduced under the portion of the surface 53 that supports the buttocks. Here heat is efficiently removed from the weight-bearing area and transferred to the cooling layer 30. FIG. 9 shows the optional thermal conducting pad layer 43 interposed between the bladder 52 and the cooling layer 30 for evening out the irregular surface caused by the channels in a water mattress that embodies the cooling layer 30.

Figure 10:
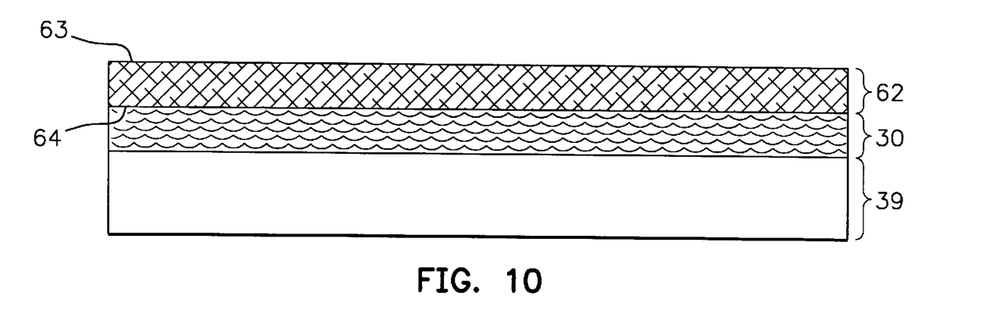
FIGS. 10 and 11 illustrate a second alternate embodiment of the invention in a longitudinal, partially schematic cross-section.
Figure 11:
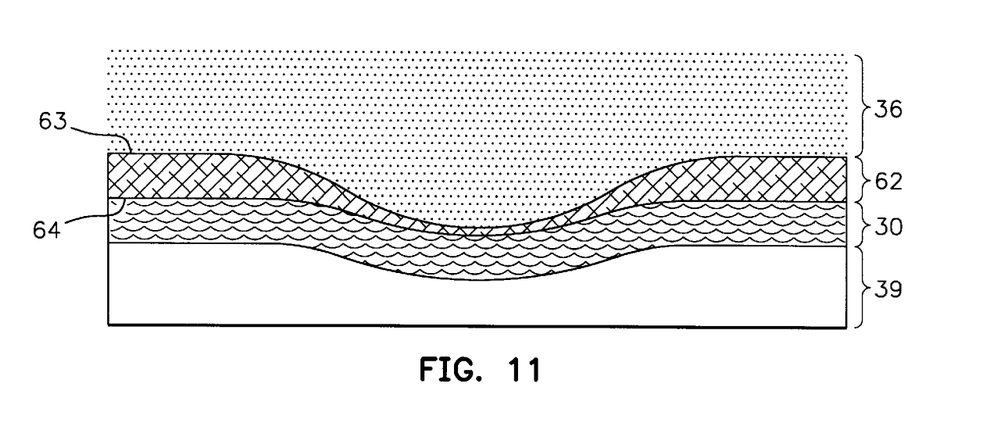
Figure 12:
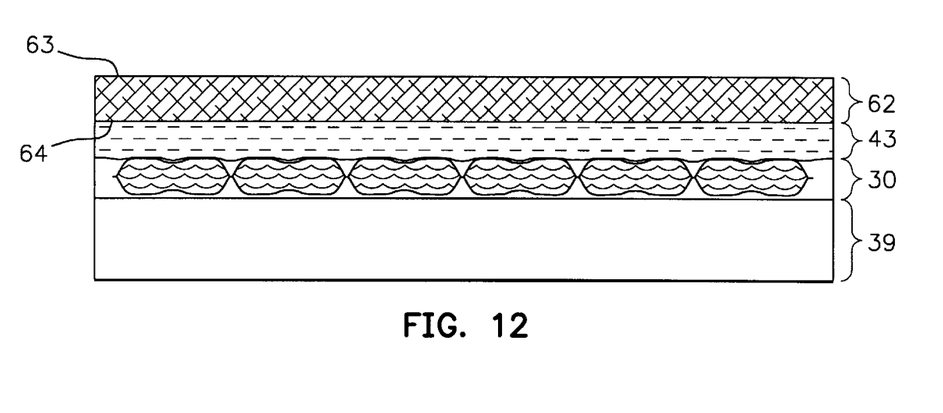
FIG. 12 illustrates an option to the second alternate embodiment in a longitudinal, partially schematic section.

A second alternate embodiment of the invention is illustrated in FIGS. 10–12. The second alternate embodiment is equivalent in all respects to the preferred embodiment except that the layer 32 of compressible, thermally insulating material is specifically embodied in a metal-wool insulating pad 62 with an upper surface 63 and a lower surface 64. The metal-wool pad is preferably a bladder made of a polymeric film or woven material, or a laminant of the two materials containing metal-wool fibers. The metal-wool material preferably is made of thinly drawn fibers of aluminum, steel, brass or other similar materials. The fibers are tangled to form a compressible pad. In its normal uncompressed state, the thickness of the metal-wool pad 62 is sufficient to provide significant thermal insulation between the surface 63 and the cooling layer 30. For example, the metal-wool pad 62 may have a thickness of between 0.5" and 2.0". As with the previously-described embodiments, the metal-wool pad 62 is compressible, exhibiting a reduced thermal resistance in those portions between the weight-bearing areas of a human body and the cooling layer 30. In the compressed state, heat conduction across the compressed metal fibers is high.

All specific embodiments of our invention have been described and exhibited in drawings for purposes of illustration, and it will be understood that many variations and alternative constructions may be made without departing from the spirit and scope of the invention which is limited only by the following claims.

We claim:

1. An apparatus for supporting a body while selectively cooling areas of the body in contact with the apparatus, comprising:

a cooling layer;

a layer of compressible, thermally insulating material disposed over the cooling layer;

a surface on the layer of compressible, thermally insulating material;

a thermally conductive material disposed in the layer of compressible, thermally insulating material and acting between the cooling layer and the layer of compressible, thermally insulating material;

the layer of compressible, thermally insulating material being responsive to pressure exerted against the surface for providing a thermal resistance between the surface and the cooling layer that varies inversely with the pressure; and means for maintaining the cooling layer at a predetermined temperature that is below normal human body temperature.

2. The apparatus of claim 1, wherein the layer of compressible, thermally insulating material comprises a foam material.

3. The apparatus of claim 2, wherein the foam material comprises a foam plastic.

4. The apparatus of claim 2, wherein the foam material comprises a foam rubber.

5. The apparatus of claim 2, wherein the layer of compressible, thermally insulating material has a thickness between the surf ace and the cooling layer of between ½ inch and 1 inch.

6. The apparatus of claim 1, wherein the cooling layer is a mattress containing a circulating fluid.

7. The apparatus of claim 1, wherein the cooling layer is contiguous with the layer of compressible, thermally insulating material.

8. The apparatus of claim 1, further including a support pad in contact with the cooling layer such that the cooling layer is sandwiched between the support pad and the layer of compressible, thermally insulating material.

9. The apparatus of claim 1, wherein the compressible, thermally insulating layer is a gas-filled pad.

10. The apparatus of claim 1, wherein the compressible, thermally insulating layer comprises a metal-wool pad.

11. The apparatus of claim 1, wherein the means for maintaining comprises a heat absorbing, phase change material.

12. The apparatus of claim 1, wherein the means for maintaining comprises a refrigerator.

13. The apparatus of claim 1 wherein the means for maintaining comprises a cooler.

14. The apparatus of claim 1, wherein the means for maintaining comprises a radiator.

15. The apparatus of claim 1, wherein the means for maintaining includes a heat exchanger.

16. The apparatus of claim 1 wherein the thermally conductive material comprises a thermally-conducting liquid.

17. A support pad for supporting a sitting or supine human body, comprising:

a cooling layer;

a layer of compressible, thermally insulating material disposed over the cooling layer;

a surface on the layer of compressible, thermally insulating material;

a thermally conductive material disposed in the layer of compressible, thermally insulating material and acting between the cooling layer and the layer of compressible, thermally insulating material;

the layer of compressible, thermally insulating material being responsive to pressure exerted against the surface for providing a thermal resistance between the surface and the cooling layer that varies inversely with the pressure; and a support pad supporting the cooling layer such that the cooling layer is between the support pad and the layer of compressible, thermally insulating material.

18. The apparatus of claim 17, wherein the layer of compressible, thermally insulating material comprises a foam material.

19. The apparatus of claim 18, wherein the foam material comprises a foam plastic.

20. The apparatus of claim 18, wherein the foam material comprises a foam rubber.

21. The apparatus of claim 18, wherein the layer of compressible, thermally insulating material has a thickness between the surface and the cooling layer of between ½ inch and 1 inch.

22. The apparatus of claim 17, wherein the cooling layer is a mattress containing a circulating fluid.

23. The apparatus of claim 17, wherein the cooling layer is contiguous with the layer of compressible, thermally insulating material.

24. The apparatus of claim 17, wherein the compressible, thermally insulating layer comprises one or more gas-filled pads.

25. The apparatus of claim 17, wherein the compressible, thermally insulating layer comprises a metal-wool pad.

\* \* \* \* \*

UNITED STATES PATENT AND TRADEMARK OFFICE
CERTIFICATE OF CORRECTION

PATENT NO. : 5,837,002
DATED : November 17, 1998
INVENTOR(S) : Augustine et al

It is certified that error appears in the above-identified patent and that said Letters Patent is hereby corrected as shown below:

On the title page: Item

[73] Assignee: Augustine Medical, Inc.

Signed and Sealed this

Fourteenth Day of September, 1999

Attest:

Q. TODD DICKINSON

*Attesting Officer*   *Acting Commissioner of Patents and Trademarks*

UNITED STATES PATENT AND TRADEMARK OFFICE
CERTIFICATE OF CORRECTION

PATENT NO. : 5,837,002
DATED : November 17, 1998
INVENTOR(S) : Augustine et al

It is certified that error appears in the above-identified patent and that said Letters Patent is hereby corrected as shown below:

Column 10, line 30
Column 10, line 32
Column 10, line 34
Column 10, line 38
Column 10, line 40
Column 10, line 43
Column 10, line 46 change "apparatus" to --support pad--.

Signed and Sealed this

Sixteenth Day of May, 2000

Attest:

Q. TODD DICKINSON

Attesting Officer

Director of Patents and Trademarks